United States Patent [19]
Moorehead

[11] 3,977,400
[45] Aug. 31, 1976

[54] CATHETER PLACEMENT UNIT WITH RESILIENT SLEEVE AND MANUAL SLEEVE CLOSURE

[75] Inventor: Harvey Robert Moorehead, Salt Lake City, Utah

[73] Assignee: Deseret Pharmaceutical Co., Inc., Sandy, Utah

[22] Filed: Nov. 29, 1974

[21] Appl. No.: 528,072

[52] U.S. Cl............................... 128/214.4; 215/311
[51] Int. Cl.²......................................... A61M 5/00
[58] Field of Search................. 128/214.4, 221, 348; 137/317, 318; 251/7; 215/311, 313, 358; 222/80, 81, 544

[56] References Cited
UNITED STATES PATENTS

| | | | |
|---|---|---|---|
| 2,797,837 | 7/1957 | Roberts | 215/311 |
| 3,459,183 | 8/1969 | Ring et al. | 128/214.4 |
| 3,766,916 | 10/1973 | Moorehead et al. | 128/214.4 |
| 3,811,440 | 5/1974 | Reading et al. | 128/214.4 |
| 3,853,127 | 12/1974 | Spademan | 128/214.4 |

FOREIGN PATENTS OR APPLICATIONS 960,889   11/1949   France

*Primary Examiner*—Dalton L. Truluck
*Attorney, Agent, or Firm*—Lynn G. Foster

[57] ABSTRACT

A catheter placement unit comprising a Y adapter with a side port for coupling a catheter tube to a fluid infusion unit and including a resilient sleeve within the axial bore of the Y adapter at the proximal end of the catheter placement unit through which a piercing needle or the like snugly passes in the initial assembled condition. A manually compressible mechanism circumscribes the resilient sleeve and, upon proper setting preferably before but also after venipuncture and needle removal, squeezes the resilient sleeve to firmly occlude the inside passage of the resilient sleeve to prevent fluid loss.

4 Claims, 7 Drawing Figures

CATHETER PLACEMENT UNIT WITH RESILIENT SLEEVE AND MANUAL SLEEVE CLOSURE

BACKGROUND

1. Field of Invention

This invention relates generally to catheter placement units and more particularly to a catheter placement unit having a Y adapter, the axial proximal end of which is closed by squeezing pressure applied to a resilient sleeve in advance of or following venipuncture and needle removal.

2. Prior Art

In the past, use of so called "resealable" plugs, diaphragms and other resilient closures in the main catheter bore at the proximal end of a catheter assembly, through which a needle or other elongated piercing element must pass, have been proposed. Too often needle removal has resulted in blood or other fluid leakage through the plug or diaphragm at the site where the needle was removed, causing utilization of such plugs and diaphragms to fall into disrepute with members of the medical profession.

BRIEF SUMMARY AND OBJECTS OF THE INVENTION

The disadvantages of the prior art are overcome by the present invention and a catheter placement unit is provided which includes a pressure applying mechanism at the proximal end thereof to squeeze a resilient member and thereby assure that the axial bore is fully occluded against fluid leakage upon removal of the piercing element.

Accordingly, it is a primary object of the present invention to provide an improved catheter placement unit.

Another paramount object of the present invention is to provide an improved catheter placement unit having pressure applying mechanism and a resilient member at the proximal end of the unit to prevent fluid leakage upon removal of the piercing element of the unit. These and other objects and features of the present invention will become apparent from the following detailed description, taken with reference to the accompanying drawings.

DETAILED DESCRIPTION OF ILLUSTRATED EMBODIMENT

Figure 1:
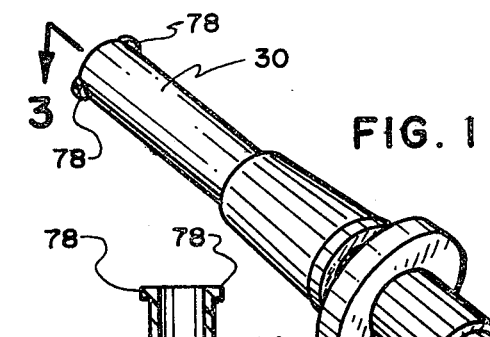
FIG. 1 is a perspective representation of a presently preferred catheter placement unit according to the present invention.

In that form of the present invention chosen for purposes of illustration, FIG. 1 depicts a catheter placement unit 10 comprising a catheter tube 12 having an axial bore 14. The distal end of the catheter tube 12 is tapered or bevelled at 16 and the other, distal end, is secured to a Y adapter 18 by a locking ring 20, the distal end of the catheter tube 12 being forced onto the forwardly divergent conically shaped distal end 22 of the Y adapter 18. Preferably, the interior of the locking ring 20 has an enlarged tapered portion 24 comprising a plurality of annular steps or shoulders. The described parts are shaped and sized so that in the illustrated assembled condition, the catheter tube 12 is firmly held in position. Epoxy resin or other suitable bonding agent may be interposed between the ring 20 and the Y adapter 18, between the catheter tube 12 and the Y adapter 18 and/or between the ring 20 and the catheter tube 12.

The Y adapter not only comprises the described reduced diameter distal end 26, but a central body 28, a side branch 30 with a side port 32. If desired, a suitable cap may be placed upon the Luer fittings 33 to close the port 32. The side port 32 communicates directly with the axial bore 34 of the Y adapter, the axial bore 34 in turn communicating with the hollow interior 14 of the catheter tube 12, when the elongated piercing element or needle 36 is removed as hereinafter more fully explained. The axial bore 34 is enlarged at 40 and there receives a cylindrically shaped resilient sleeve 42, the outside diameter of which is essentially the same as the inside diameter of the Y adapter 18 at location 40 and the inside diameter of which is the same or slightly less than the diameter of the piercing member 36 so that the piercing member passes snugly through the interior bore 44 of the resilient sleeve 42.

Figure 2:
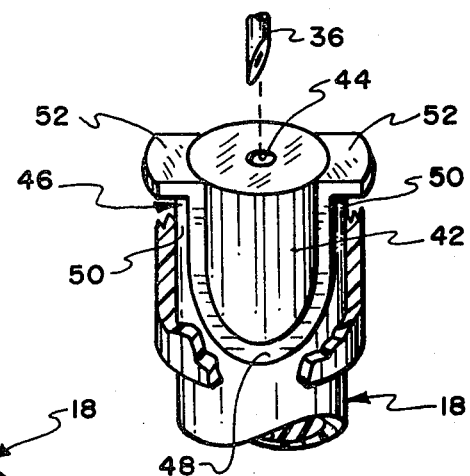
FIG. 2 is an enlarged fragmentary perspective with parts broken away for clarity of the pressure applying mechanism and resilient sleeve found at the proximal end of a Y adapter comprising the catheter placement unit of FIG. 1 showing the piercing element removed.
Figures 3, 4:
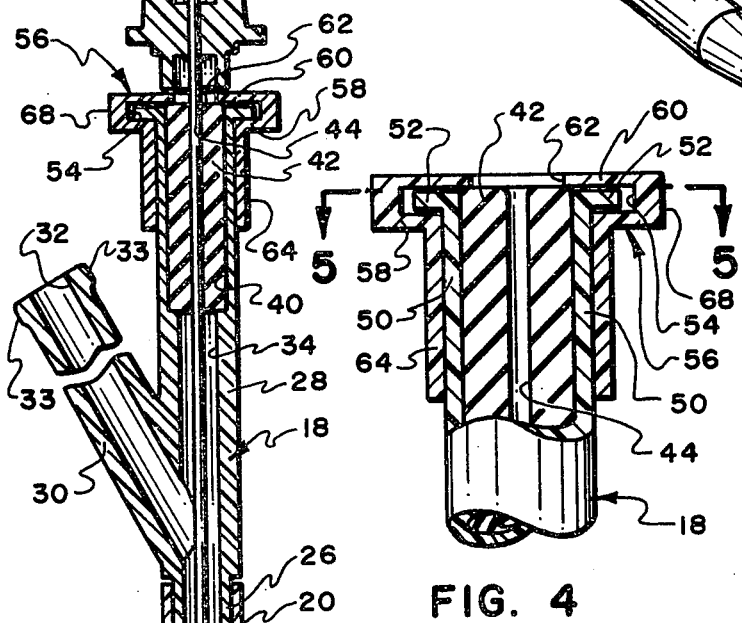
FIG. 3 is a longitudinal cross section of the catheter placement unit of FIG. 1 taken along line 3—3 thereof.
FIG. 4 is an enlarged fragmentary cross section of the pressure applying mechanism and resilient sleeve disposed on the proximal end of the axial bore of the Y adapter shown in the open condition, with the piercing needle removed.

The proximal end of the Y adapter 18 comprises a modified hub, as best illustrated in FIG. 2. The cylindrical wall of the axial bore 28 at hub portion 46 comprises a pair of oppositely disposed U recesses 48, separated by opposed resilient fingers 50, which are readily deflected against the resilient sleeve 42. The fingers respectively terminate in radially directed dogs 52 which are disposed 180° from each other and extend in opposite directions.

The dogs 52 are confined within an irregularly shaped groove 54 of a pressure applying cap 56, which is rotatably disposed upon the proximal end 46 of the Y adapter 18. Radial walls 58 and 60 define the front and back of the groove 54, wall 60 providing a central aperture 62 through which the piercing element 36 passes. A hollow cylindrical shank 64, the inside diameter of which is essentially the same as the outside diameter of the proximal end 46 of the Y adapter 18 aligns the pressure applying mechanism 56 with the remainder of the catheter placement unit 10.

Figure 5:
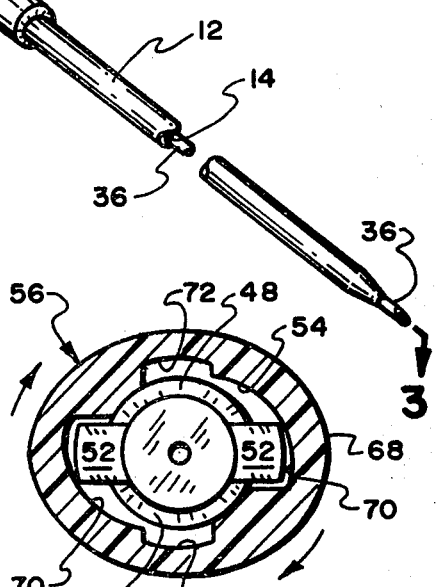
FIG. 5 is a cross section taken along line 5—5 of FIG. 4.
Figure 6:
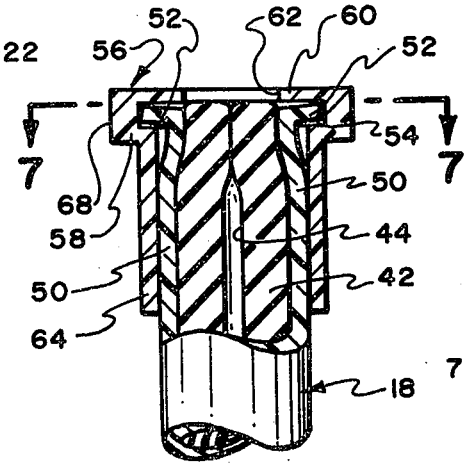
FIG. 6 is a fragmentary cross section similar to FIG. 4 with the pressure applying mechanism closed to occlude the central bore of the resilient sleeve.
Figure 7:
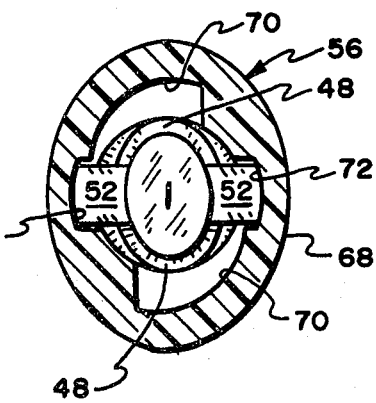
FIG. 7 is a cross sectional view taken along line 7—7 of FIG. 6.

The peripheral configuration of the groove 54 of the pressure applying mechanism 56 is best illustrated in FIGS. 5 and 7. Clearly, the external configuration at periphery 68 is eliptical or oblong. Internally, the groove 54 comprises tapered slots 70 and locking recesses 72. When no pressure is being applied by the mechanism 56, the dogs 52 rest in the maximum diameter portion of tapered open grooves 70. As the pressure applying cap mechanism 56 is manually twisted in a clockwise direction as illustrated in FIG. 5, the dogs 52 will be engaged by the walls of open grooves 70 causing the dogs 52 and connected fingers 50 to be deflected toward the resilient sleeve 42. Once the clockwise rotation has occurred sufficient to displace the dogs 52 relative to the open tapered grooves 70 slightly beyond the midpoint thereof, the central bore 44 of the resilient sleeve 42 will be occluded, either before or after removal of the piercing element 36. The cap pressure applying mechanism 56 may be left in the indicated position, if it is desired to reopen the bore 44 of the sleeve 42 for some reason. In most instances, however, it is desired to prevent subsequent opening of the bore 44. Thus, the clockwise rotation of the cap 56 is continued until the dogs 52 lock firmly in the recesses of 72, which are sized, shaped and dimensioned to maintain total occlusion of the bore 44 of the sleeve 42 and which prevent inadvertent opening of the bore 44. The described position wherein the pressure applying cap 56 totally occludes in locked condition the bore 44 of the sleeve 42 as illustrated in FIGS. 6 and 7.

The proximal end of the piercing element 32 is anchored by epoxy resin or other suitable bonding agent to a hub 74. The hub 74 comprises a hollow venipuncture chamber 76, the material of the hub 74 being preferably transparent to provide a visual indication of flashback at chamber 76 following venipuncture. The chamber 76 may be capped in a conventional way utilizing the Luer dogs 78. Obviously, the hub 74 is manually gripped by the user to remove the hub 74 and the piercing element 36 following venipuncture. Also, a fluid infusion device may be attached to the hub 74 at Luer dog 78 to initially infuse fluid into the patient upon venipuncture, if desired.

Preferably before, but if desired after venipuncture and needle removal, the axial bore of the Y adapter 18 is closed by using the cap pressure applying mechanism 56 in the manner described. Thereafter, the Y catheter is utilized with the patient in a conventional manner.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A catheter assembly comprising:
    a catheter tube having an axial bore;
    elongated piercing means coaxially disposed through and extending beyond the leading end of the axial bore of the catheter tube;
    a female hub on the trailing end of the catheter tube;
    a resilient sleeve member disposed within the female hub and having a bore therethrough through which the piercing means contiguously passes prior to venipuncture;
    mechanical means disposed on the female hub in radial alignment with the site where the piercing means and the resilient sleeve member are contiguous, the mechanical means comprising movable means and opposed pressure applying means associated with the said hub and resilient sleeve number whereby selective movement of the movable means manually repositions the pressure applying means, before or after venipuncture and removal of the piercing means, to constrict the resilient member at said site to fully occlude any passageway in the resilient member at said site thereby preventing fluid leakage across the resilient member and opposed locking means retaining the movable means in said occluding position.

2. The catheter assembly of claim 1 wherein the female hub comprises the proximal portion of a Y adapter.

3. The catheter assembly of claim 1 wherein the piercing means comprises a hollow needle having a flashback chamber attached thereto proximal of the female hub.

4. The catheter assembly of claim 1 wherein the pressure applying means comprise opposed radially yieldable fingers adjacent the resilient sleeve member at said site and opposed radial dogs each attached to one of the fingers, and wherein the opposed locking means comprise a rotatable cap mounted to the proximal of the hub receiving the dogs in an eccentrically configurated groove, whereby rotation of the cap causes groove surfaces to engage the dogs and oppositely compress the fingers against the resilient sleeve member at said site for full occlusion.

* * * * *